(12) United States Patent
Kondo (10) Patent No.: US 9,139,533 B2
(45) Date of Patent: Sep. 22, 2015

(54) CAPSULE-TYPE COMPOUND, ANION REMOVING AGENT, AND METHOD FOR REMOVING ANION

(75) Inventor: Mitsuru Kondo, Shizuoka (JP)

(73) Assignee: NATIONAL UNIVERSITY CORPORATION SHIZUOKA UNIVERSITY, Shizuoka-shi (JP)

(*) Notice: Subject to any disclaimer, the term of this patent is extended or adjusted under 35 U.S.C. 154(b) by 151 days.

(21) Appl. No.: 13/980,988

(22) PCT Filed: Jan. 26, 2012

(86) PCT No.: PCT/JP2012/051720
§ 371 (c)(1),
(2), (4) Date: Jul. 22, 2013

(87) PCT Pub. No.: WO2012/102356
PCT Pub. Date: Aug. 2, 2012

(65) Prior Publication Data
US 2013/0299431 A1  Nov. 14, 2013

(30) Foreign Application Priority Data

Jan. 28, 2011 (JP) .................... 2011-016235

(51) Int. Cl.
C02F 1/42 (2006.01)
C07D 235/20 (2006.01)
C07F 1/00 (2006.01)

(52) U.S. Cl.
CPC ............... *C07D 235/20* (2013.01); *C02F 1/42* (2013.01); *C07F 1/005* (2013.01); *C02F 2001/422* (2013.01)

(58) Field of Classification Search
USPC ........................................................ 210/683
See application file for complete search history.

(56) References Cited

U.S. PATENT DOCUMENTS

2010/0200508 A1  8/2010  Kondo

FOREIGN PATENT DOCUMENTS

| EP | 2 067 774 A1 | 6/2009 |
| JP | 2004346299 A | 12/2004 |

(Continued)

OTHER PUBLICATIONS

Su, Cheng-Yong, et al., "Coordination-directed assembly of trigonal and tetragonal molecular boxes encapsulating anionic guests," J. Chem. Soc., Dalton Trans., 2001, 359-361.*

(Continued)

*Primary Examiner* — Chester Barry
(74) *Attorney, Agent, or Firm* — Marshall, Gerstein & Borun LLP (57) ABSTRACT

The present invention provides a capsule-type compound consisting of:
a capsule-type divalent cation consisting of a capsule framework represented by the following formula (1) and a sulfate ion ($SO_4^{2-}$) encapsulated in the capsule framework; and a sulfate ion ($SO_4^{2-}$) as a counter ion to the capsule-type divalent cation. In the formula (1), $R^1$, $R^2$, $R^3$, $R^4$, $R^5$, $R^6$, $R^7$, $R^8$, $R^9$, $R^{10}$, $R^{11}$, $R^{12}$, and $R^{13}$ each independently represent a hydrogen atom or a methyl group; and $M^1$ and $M^2$ each independently represent $Cu^{2+}$, $Fe^{2+}$, $Ni^{2+}$, $Co^{2+}$, or $Zn^{2+}$.

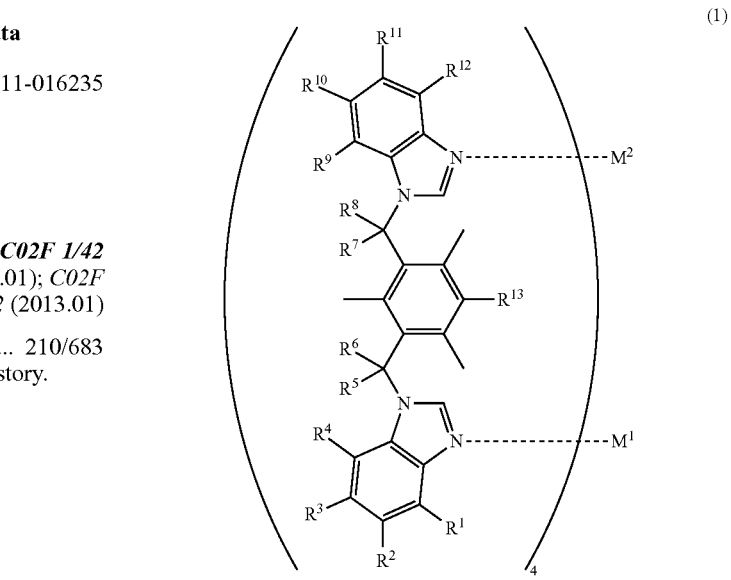

7 Claims, 7 Drawing Sheets

(56) References Cited

FOREIGN PATENT DOCUMENTS

| | | |
|---|---|---|
| JP | 2010022886 A | 2/2010 |
| JP | 2010042403 A | 2/2010 |
| WO | WO-2008029804 A1 | 3/2008 |

OTHER PUBLICATIONS

Su et al., "Ligand-Directed Molecular Architectures: Self-Assembly of Two-Dimensional Rectangular Metallacycles and Three-Dimensional Trigonal or Tetragonal Prisms," *J. Am. Chem. Soc.*, 125:8595-8613 (2003).

NEDO Foreign Report No. 946, Dec. 15, 2004, "System for Eliminating Perchlorate Salt That Supports Identification of Sources of Contamination."

International Search Report for PCT/JP2012/051720 dated Jan. 26, 2012.

Su et al., "Columnar Supramolecular Architecture Self-Assembled from $S_4$-Symmetric Coordination Nanotubes Encapsulating Neutral Guest Molecules", Angew. Chem. Int. Ed., 42, 2003, pp. 4085-4089.

Su et al., "Coordination-Directed Assembly of Trigonal and Tetragonal Molecular Boxes Encapsulating Anionic Guests", J. Chem. Soc., Dalton Trans., 2001, pp. 359-361.

Desmarets et al., Design, Self-Assembly, and Molecular Structures of 3D Copper(II) Capsules Templated by $BF_4$ Guest Anions, Eur. J. Inorg. Chem., 2009, pp. 4396-4400.

Extended European Search Report in EP Application No. 12740009.1 dated May 27, 2014.

* cited by examiner

FIG.1

$[SO_4 \subset Cu_2(m-bbitb)_4]SO_4$

CAPSULE-TYPE COMPOUND, ANION REMOVING AGENT, AND METHOD FOR REMOVING ANION

TECHNICAL FIELD

The present invention relates to a capsule-type compound, an anion removing agent, and a method for removing an anion.

BACKGROUND ART

A perchlorate ion ($ClO_4^-$), a tetrafluoroborate ion ($BF_4^-$), a nitrate ion ($NO_3^-$), and a bromide ion ($Br^-$) have high solubility in water, although being harmful ions, and are therefore anions that are difficult to remove from aqueous solutions. In addition to the anions, an iodide ion ($I^-$) also has high solubility in water and is an anion that is difficult to remove from aqueous solutions.

For example, it has been feared that perchlorate ions cause infants and children to develop growth impairment or intellectual impairment by being ingested in excess.

As a method for removing an anion such as a perchlorate ion from an aqueous solution, for example, a method using an ion exchange resin has been known (for example, see Japanese Patent Application Laid-Open (JP-A) No. 2004-346299 and "NEDO Foreign Report, No. 946, 2004.12.15").

Further, there has been known a method of producing a trapping capsule type molecule with a structure in which a perchlorate ion is encapsulated in a capsule framework consisting of four molecules of bitb and two $Cu^{2+}$ ions by adding 1,4-bis(imidazol-1-yl-methyl)2,3,5,6-tetramethylbenzene (hereinafter also referred to as "bitb") to an aqueous solution containing the perchlorate ion and precipitating the produced trapping capsule type molecule (for example, see International Publication No. WO 2008/029804 pamphlet). It has been known that bitb exhibits the effect of removing other anions such as a tetrafluoroborate ion ($BF_4^-$) as well as the perchlorate ion ($ClO_4^-$) (for example, see Japanese Patent Application Laid-Open (JP-A) No. 2010-022886 and Japanese Patent Application Laid-Open (JP-A) No. 2010-042403).

SUMMARY OF INVENTION

Technical Problem

However, it is demanded to more efficiently decrease the concentration of at least one anion selected from the group consisting of $ClO_4^-$, $BF_4^-$, $NO_3^-$, $Br^-$, and $I^-$ in a water-based sample in a shorter time.

Thus, an object of the present invention is to provide a capsule-type compound, an anion removing agent, and a method for removing an anion, wherein, in a water-based sample containing at least one anion selected from the group consisting of $ClO_4^-$, $BF_4^-$, $NO_3^-$, $Br^-$, and $I^-$ as well as water, the concentration of the anion can be efficiently decreased in a short time.

Means for Solving the Problem

Means for solving the problems are as follows:
<1> A capsule-type compound consisting of: a capsule-type divalent cation consisting of a capsule framework represented by the following formula (1) and a sulfate ion ($SO_4^{2-}$) encapsulated in the capsule framework; and a sulfate ion ($SO_4^{2-}$) as a counter ion to the capsule-type divalent cation.

(1)

wherein, in the formula (1), $R^1$, $R^2$, $R^3$, $R^4$, $R^5$, $R^6$, $R^7$, $R^8$, $R^9$, $R^{10}$, $R^{11}$, $R^{12}$ and $R^{13}$ each independently represent a hydrogen atom or a methyl group. In the formula (1), $M^1$ and $M^2$ each independently represent $Cu^{2+}$, $Fe^{2+}$, $Ni^{2+}$, $Co^{2+}$, or $Zn^{2+}$. In the formula (1), a broken line represents a coordinate bond.

<2> The capsule-type compound according to <1>, wherein $M^1$ and $M^2$ are the same.

<3> The capsule-type compound according to <1> or <2>, wherein $M^1$ and $M^2$ are $Cu^2$.

<4> The capsule-type compound according to any one of <1> to <3>, wherein $R^1$, $R^2$, $R^3$, $R^4$, $R^5$, $R^6$, $R^7$, $R^8$, $R^9$, $R^{10}$, $R^{11}$, $R^{12}$, and $R^{13}$ are all hydrogen atoms.

<5> An anion removing agent including, as an active component, the capsule-type compound according to any one of <1> to <4>.

<6> A method for removing an anion, comprising a step of bringing a water-based sample containing at least one anion selected from the group consisting of $ClO_4^-$, $BF_4^-$, $NO_3^-$, $Br^-$, and $I^-$ as well as water, and the capsule-type compound according to any one of <1> to <4> into contact with each other to remove the anion from the water-based sample.

<7> The method for removing an anion according to <6>, wherein the water-based sample contains at least $ClO_4^-$.

Effects of Invention

In accordance with the present invention, there can be provided a capsule-type compound, an anion removing agent, and a method for removing an anion, wherein, in a water-based sample containing at least one anion selected from the group consisting of $ClO_4^-$, $BF_4^-$, $NO_3^-$, $Br^-$, and $I^-$ as well as water, the concentration of the anion can be efficiently decreased in a short time.

DESCRIPTION OF EMBODIMENTS

Capsule-Type Compound

The capsule-type compound of the present invention is a compound consisting of: a capsule-type divalent cation consisting of a capsule framework represented by the following formula (1) and a sulfate ion (SO$_4^{2-}$) encapsulated in the capsule framework; and a sulfate ion (SO$_4^{2-}$) as a counter ion to the capsule-type divalent cation.

(1)

In the formula (1), $R^1$, $R^2$, $R^3$, $R^4$, $R^5$, $R^6$, $R^7$, $R^8$, $R^9$, $R^{10}$, $R^{11}$, $R^{12}$, and $R^{13}$ each independently represent a hydrogen atom or a methyl group. In the formula (1), $M^1$ and $M^2$ each independently represent Cu$^{2+}$, Fe$^{2+}$, Ni$^{2+}$, Co$^{2+}$, or Zn$^{2+}$. In the formula (1), a broken line represents a coordinate bond.

Figure 1:
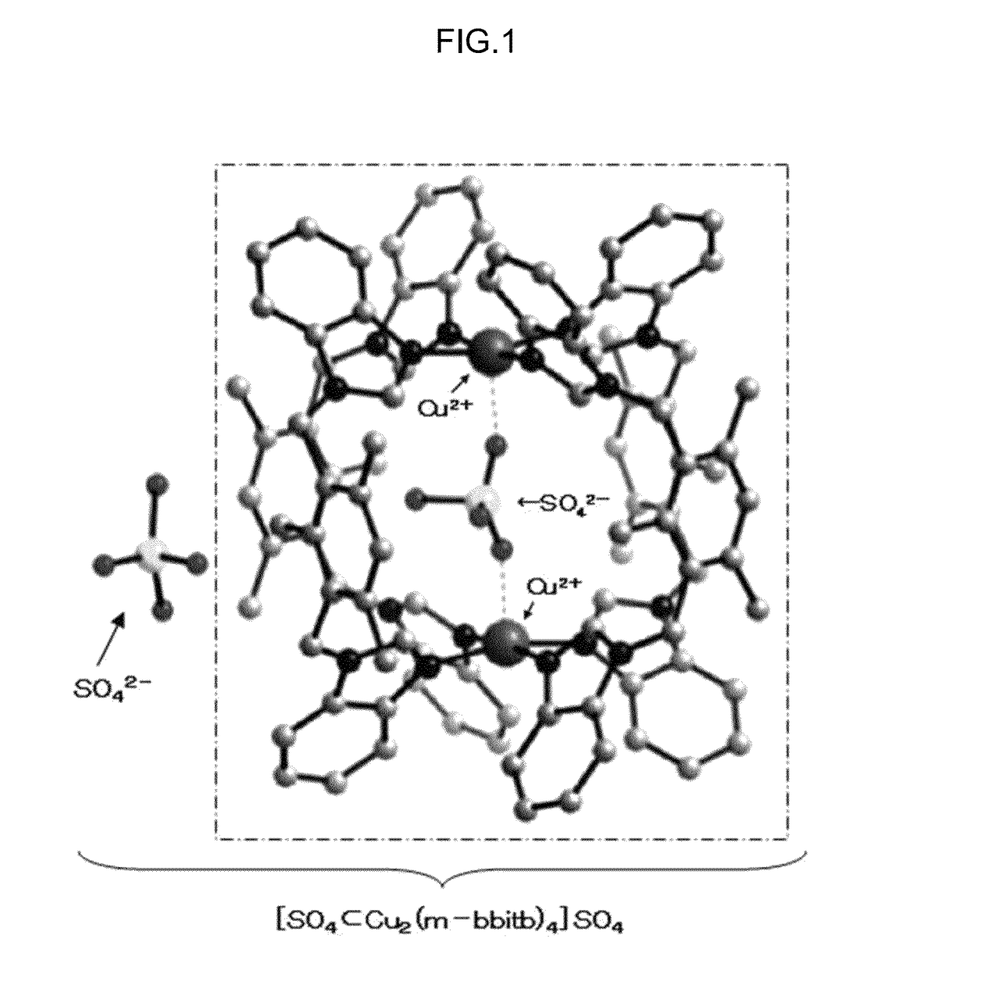
FIG. 1 is a molecular structure view of a capsule-type compound "[$SO_4 \subset Cu_2(m\text{-}bbitb)_4$]$SO_4$" which is an example of the capsule-type compound of the present invention.

FIG. 1 is a molecular structure view that conceptually illustrates a capsule-type compound in which $R^1$ to $R^{13}$ in the formula (1) and the formula (2) described below are hydrogen atoms and $M^1$ and $M^2$ in the formula (1) are Cu$^{2+}$, as an example of the capsule-type compound of the present invention.

The compound in which $R^1$ to $R^{13}$ in the formula (2) described below are hydrogen atoms is 1,3-bis(benzimidazol-1-yl-methyl)-2,4,6-trimethylbenzene (hereinafter also referred to as "m-bbitb").

Further, in the specification, the capsule-type compound in which $R^1$ to $R^{13}$ in the formula (1) are hydrogen atoms and $M^1$ and $M^2$ in the formula (1) are Cu$^{2+}$ also refers to "[SO$_4 \subset$ Cu$_2$(m-bbitb)$_4$]SO$_4$".

As illustrated in FIG. 1, the structure of [SO$_4 \subset$ Cu$_2$(m-bbitb)$_4$]SO$_4$ is a structure consisting of: a capsule-type divalent cation consisting of a capsule framework formed with two Cu$^{2+}$ ions and four molecules of m-bbitb and one sulfate ion (SO$_4^{2-}$) encapsulated in the capsule framework (moiety surrounded by an alternate long and short dash line in FIG. 1); and one sulfate ion (SO$_4^{2-}$) as a counter ion to the capsule-type divalent cation. Two oxygen atoms in the encapsulated sulfate ion (SO$_4^{2-}$) are each coordinate-bonded to two Cu$^{2+}$ ions as indicated by broken lines in FIG. 1.

The capsule-type divalent cation is constituted as a divalent cation as a whole by two Cu$^{2+}$ ions, one sulfate ion (SO$_4^{2-}$), and four molecules of m-bbitb. [SO$_4 \subset$ Cu$_2$(m-bbitb)$_4$]SO$_4$ is constituted as a neutral compound as a whole by the capsule-type divalent cation and one sulfate ion (SO$_4^{2-}$) as a counter ion.

The structure illustrated in FIG. 1 can be confirmed by single-crystal structure analysis.

The structure of the capsule-type compound of the present invention other than [SO$_4 \subset$ Cu$_2$(m-bbitb)$_4$]SO$_4$ is the same as the structure of [SO$_4 \subset$ Cu$_2$(m-bbitb)$_4$]SO$_4$ except the kind of a ligand (compound in the parentheses in the formula (1)) and the kind of a metal ion.

Contact between the capsule-type compound of the present invention and a water-based sample containing at least one anion selected from the group consisting of ClO$_4^-$, BF$_4^-$, NO$_3^-$, Br$^-$, and I$^-$ as well as water causes immediate counterion-exchange between the anion and a sulfate ion as a counter ion in the capsule-type compound of the present invention. Therefore, the anion in the water-based sample is incorporated into the capsule-type compound as a counter ion.

Thus, in accordance with the capsule-type compound of the present invention, the concentration of the anion in the water-based sample can be efficiently decreased in a short time.

Both of the capsule-type compound of the present invention and the capsule-type compound subjected to the counterion-exchange are insoluble in water, and it is considered that the insolubility also contributes to the efficient decrease in the concentration of the anion in a short time.

Furthermore, the capsule-type compound of the present invention is insoluble in water and therefore has an advantage that the concentration of the anion can be decreased while suppressing the contamination of the water-based sample in the state of being suspended in the water-based sample.

As used herein, the phrase "insoluble in water" refers to a solubility of 0.1 part by mass or less with respect to 100 parts by mass of water (25° C.).

Furthermore, the concentration of the anion in the water-based sample can be efficiently decreased in a short time using the capsule-type compound of the present invention, in comparison with a method for removing an anion (perchlorate ion) using 1,4-bis(imidazol-1-yl-methyl)2,3,5,6-tetramethylbenzene (bitb) described in International Publication No. WO 2008/029804 pamphlet. The reason thereof is presumed as described below.

In other words, in the method described in the pamphlet, it is necessary to add bitb into a water-based sample containing a perchlorate ion and water to produce a trapping capsule type molecule with a structure in which the perchlorate ion is encapsulated in a capsule framework consisting of four molecules of bitb and two Cu$^{2+}$ ions.

In contrast, the use of the capsule-type compound of the present invention does not require the formation of a capsule structure with the formation of a strong chemical bond such as a coordinate bond between a metal and a ligand. This is because, by adding the capsule-type compound of the present invention into a water-based sample containing an anion such as a perchlorate ion and water, the anion is removed from the water-based sample by counterion exchange.

Therefore, shorter reaction time in the counterion exchange in the use of the capsule-type compound of the present invention than reaction time in the production of the trapping capsule type molecule in the method described in the above-described pamphlet is presumed to contribute to more efficient removal of an anion in a shorter time.

However, the present invention is not limited by the above-described reason.

Thus, the decrease in the concentration of the anion in the water-based sample by the capsule-type compound of the present invention does not require a long time (for example, 1 hour or more), and further, does not require particular limitation of the concentration of the anion in the water-based sample prior to treatment (prior to treatment with the capsule-type compound of the present invention; the same applies hereafter). Thus, for example, a water-based sample in which the concentration of the anion is 20 mM or less may also be used as the water-based sample prior to the treatment.

Further, time required for decreasing the concentration of the anion in the water-based sample by the capsule-type compound of the present invention may be, for example, 30 minutes or less, further 10 minutes or less, or further 5 minutes or less.

Further, when the concentration of the anion in the water-based sample is decreased by the capsule-type compound of the present invention, the concentration of the anion in the water-based sample prior to treatment may be, for example, 10 mM or less, further 5 mM or less, or further 1 mM or less.

The capsule-type compound of the present invention allows the concentration of particularly $ClO_4^-$ among the anions to be remarkably (i.e., more efficiently and in a shorter time) decreased.

"Water-based sample" in the present invention is not particularly limited as long as the sample contains at least water as a solvent.

As "water-based sample", a water-based sample in which the ratio of water in a solvent is 30 mass % or more is preferred, a water-based sample in which the ratio of water in a solvent is 50 mass % or more is more preferred, and a water-based sample in which the ratio of water in a solvent is 80 mass % or more is further preferred.

The water-based sample of the present invention may optionally contain, as a solvent, at least one of polar protic solvents (such as methanol, ethanol, 1-propanol, 2-propanol, 1-butanol, acetic acid, and formic acid), polar aprotic solvents (such as tetrahydrofuran, acetone, acetonitrile, dimethylformamide, and dimethyl sulfoxide), and nonpolar solvents (such as benzene, hexane, toluene, diethyl ether, chloroform, ethyl acetate, and methylene chloride), as well as water.

Specific examples of "water-based sample" in the present invention include, e.g., clean water, sewage, various wastewaters (such as industrial wastewater), liquid intermediate products, industrial water, drinkable water, various aqueous solutions, colloidal solutions (such as milk), suspensions containing a food product or soil, and the like.

Further, $M^1$ and $M^2$ in the formula (1) are preferably cations of the same kind from the viewpoint of easiness of synthesis or the like. Furthermore, $M^1$ and $M^2$ are particularly preferably $Cu^{2+}$ in view of allowing the concentration of an anion to be decreased in a shorter time.

In accordance with the present invention, the compound in the parentheses in the formula (1) is also referred to as a ligand.

The ligand in the present invention is a compound represented by the following formula (2).

(2)

$R^1$ to $R^{13}$ in the formula (2) are synonymous with $R^1$ to $R^{13}$ in the formula (1).

$R^1$ to $R^{12}$ in the formulae (1) and (2) are preferably hydrogen atoms from the viewpoint of easiness of synthesis or the like. Furthermore, $R^1$ to $R^{13}$ in the formulae (1) and (2) are preferably hydrogen atoms from the viewpoint of easiness of synthesis.

Examples of methods for synthesizing the compound represented by the formula (2) include a synthesis method described in H. K. Liu, C. Y. Su, C. M. Qian, J. Liu, H. Y. Tan, B. S. Kang, J. Chem. Soc., DaltonTrans., 2001, 8, 1167.

Exemplary compounds of the compound represented by the formula (2) are illustrated below. However, the present invention is not limited thereto.

The following exemplary compound (a) is 1,3-bis(benzimidazol-1-yl-methyl)-2,4,6-trimethylbenzene (m-bbitb).

(a)

(b)

(c)

(d)

Further, examples of methods for synthesizing the capsule-type compound of the present invention include a method of reacting a sulfate containing at least one of $Cu^{2+}$, $Fe^{2+}$, $Ni^{2+}$, $Co^{2+}$, and $Zn^{2+}$ with the compound represented by the formula (2) in water (or an aqueous solvent containing water). As a result, the capsule-type compound of the present invention can be obtained as a compound (precipitate) insoluble in water.

Reaction temperature in the reaction is not particularly limited but is preferably, for example, from 10° C. to 80° C.

Reaction time is not also particularly limited but is preferably 20 minutes or more.

<<Anion Removing Agent>>

The anion removing agent of the present invention includes, as an active component, the above-described capsule-type compound of the present invention.

Therefore, by bringing the anion removing agent of the present invention and a water-based sample containing at least one anion selected from the group consisting of $ClO_4^-$, $BF_4^-$, $NO_3^-$, $Br^-$, and $I^-$ as well as water into contact with each other, the concentration of the anion in the water-based sample can be efficiently decreased in a short time.

Examples of a first embodiment of the anion removing agent of the present invention include an embodiment of a simple substance of the capsule-type compound of the present invention in a solid state (such as powder or crystal form).

Further, examples of a second embodiment of the anion removing agent of the present invention include an embodiment of a mixture (tablet form or the like) of the capsule-type compound of the present invention in a solid state and another component such as a binder component.

Further, examples of a third embodiment of the anion removing agent of the present invention include an embodiment of a suspension in which the capsule-type compound of the present invention (or a mixture containing the capsule-type compound according to the present invention) is suspended in a water-based medium.

<<Method for Removing Anion>>

The method for removing an anion of the present invention includes the step of bringing a water-based sample containing at least one anion selected from the group consisting of $ClO_4^-$, $BF_4^-$, $NO_3^-$, $Br^-$, and $I^-$ as well as water, and the above-described capsule-type compound of the present invention into contact with each other to remove the anion from the water-based sample.

According to the method for removing an anion of the present invention, the concentration of the anion in the water-based sample can be efficiently decreased in a short time since the capsule-type compound of the present invention and the anion can be brought into contact with each other.

The contact between the water-based sample and the capsule-type compound of the present invention can be caused by, for example, adding the capsule-type compound of the present invention (or the anion removing agent including, as an active component, the capsule-type compound of the present invention) into the water-based sample. The contact may also be caused by putting the capsule-type compound of the present invention (or the anion removing agent including, as an active component, the capsule-type compound of the present invention) in a container beforehand and by adding the water-based sample thereinto.

Further, it is also preferable to cause the contact by passing the water-based sample through a filter on which the capsule-type compound of the present invention (or the anion removing agent including, as an active component, the capsule-type compound of the present invention) is fixed.

While the water-based sample in the present invention includes at least one anion selected from the group consisting of $ClO_4^-$, $BF_4^-$, $NO_3^-$, $Br^-$, and $I^-$, a more preferred embodiment of the water-based sample is an embodiment in which at least one anion selected from the group consisting of $ClO_4^-$, $BF_4^-$, $NO_3^-$, and $Br^-$ is included.

Furthermore, since the capsule-type compound of the present invention particularly allows the concentration of $ClO_4^-$ to be remarkably (more efficiently in a short time) decreased, it is preferable that the water-based sample contains at least $ClO_4^-$. In other words, it is preferable that the water-based sample contains at least $ClO_4^-$ and further optionally contains at least one anion selected from the group consisting of $BF_4^-$, $NO_3^-$, $Br^-$, and $I^-$.

In the method for removing an anion of the present invention, the water-based sample may also be heated from the viewpoint of increasing the frequency of contact between the capsule-type compound of the present invention and the anion.

Temperature at the time of the contact may be from 0° C. to 100° C. and is preferably from 20° C. to 80° C.

In the method for removing an anion, the water-based sample may be stirred or may be left without stirring, after the contact between the capsule-type compound of the present invention and the anion, and is preferably stirred from the viewpoint of increasing the frequency of the contact.

For the stirring, means such as a stirrer, shaking of a container, irradiation with ultrasonic waves, irradiation with microwaves, or convection by heating may be used. Especially, irradiation with ultrasonic waves is preferred.

Since the ion-exchanged capsule-type compound generated by the method for removing an anion of the present invention is insoluble in water, the anion can be easily separated from the water-based sample.

As a separation method, a usual method of separating a precipitate from a solution can be applied without being changed, and examples thereof may include separation by decanting supernatant liquid, filtration with a filter, separation by a centrifugation operation, and the like.

In the method for removing an anion of the present invention, a sulfate ion ($SO_4^{2-}$) which is less harmful in comparison with $ClO_4^-$, $BF_4^-$, $NO_3^-$, $Br^-$, and $I^-$ is released into the water-based sample by the counterion exchange of the sulfate ion which is a counter ion in the capsule-type compound of the present invention with the anion to be removed.

The released sulfate ion can be easily removed from the water-based sample by a known method such as a method of precipitating the sulfate ion as a salt that is very slightly soluble in water by adding calcium chloride.

In the method for removing an anion of the present invention, the ion-exchanged capsule-type compound generated by removing the anion is decomposed to produce a ligand (compound represented in the formula (2)) and the capsule-type compound of the present invention can be synthesized (reproduced) using the produced ligand. The decomposition can be caused by a method of extracting the ion-exchanged capsule-type compound with an organic solvent such as methanol and adding, to resultant extraction liquid, a solution in which a basic reagent such as sodium carbonate is dissolved; a method of passing hydrogen sulfide through the extraction liquid; or the like.

EXAMPLES

Examples of the present invention will be explained below, but the present invention is not limited to the examples. In the examples described below, ion-exchanged water was used as any water used for preparing a solution or measuring.

Example 1

Synthesis of 1,3-bis(benzimidazol-1-yl-methyl)-2,4,6-trimethylbenzene (m-bbitb)

1,3-Bis(benzimidazol-1-yl-methyl)-2,4,6-trimethylbenzene (m-bbitb) was synthesized according to the synthesis method described in H. K. Liu, C. Y. Su, C. M. Qian, J. Liu, H. Y. Tan, B. S. Kang, J. Chem. Soc., Dalton Trans., 2001, 8, 1167.

Synthesis of Capsule-Type Compound ([$SO_4 \subset Cu_2$(m-bbitb)$_4$]$SO_4$)

A capsule-type compound ([$SO_4 \subset Cu_2$(m-bbitb)$_4$]$SO_4$) was synthesized according to the following reaction scheme 1.

-Reaction Scheme 1-

A detailed description will now be made of the reaction scheme 1.

First, $CuSO_4 \cdot 5H_2O$ (37 mg, 0.15 mmol) was dissolved in water (30 mL) to obtain an aqueous solution of $CuSO_4 \cdot 5H_2O$.

Then, an m-bbitb solution in which m-bbitb (110 mg, 0.30 mmol) was dissolved in ethanol was prepared, the obtained m-bbitb solution was added to the aqueous solution of $CuSO_4 \cdot 5H_2O$, and the resultant was left standing at room temperature (25° C.) for around 1 week to yield a blue solid.

The obtained blue solid was filtrated, collected, and dried to obtain [$SO_4 \subset Cu_2$(m-bbitb)$_4$]$SO_4$ with the structure illustrated in FIG. 1 (yield of 98.1 mg (yield of 66.4%)).

The structure of [$SO_4 \subset Cu_2$(m-bbitb)$_4$]$SO_4$ was confirmed by the following elemental analysis and the following crystallographic data (single-crystal X-ray structure analysis).

The elemental analysis was conducted using Euro EA3000 manufactured by Euro Vector.

The single-crystal X-ray structure analysis was conducted by collecting X-ray reflectance data using a structural analyzer (mercury two-dimensional detector system) manufactured by Rigaku Corporation and using molybdenum Kα radiation source at room temperature (25° C.), and by analyzing the collected reflectance data using a Crystal Structure program manufactured by Rigaku Corporation.

—Elemental Analysis Results—

Calcd. for $C_{100}H_{110}Cu_2N_{16}O_{15}S_2$: C, 61.05; H, 5.64; N, 11.39.

Found: C, 60.66; H, 5.21; N, 11.07.

—Crystallographic Data—

Molecular formula: $C_{100}H_{110}Cu_2N_{16}O_{15}S_2$, $M_r$=1967.28, monoclinic, space group C2/m (No. 12), a=19.508 (15) Å, b=24.484 (19) Å, c=13.377 (11) Å, β=126.072 (7)°, V=5164 (7) Å$^3$, Z=2, $D_c$=1.265 gcm$^{-3}$, μ(Mo Kα)=0.521 mm$^{-1}$, T=293 K, λ=0.7107 Å, ω scan. Of a total of 5935 reflections collected, 3450 were independent ($R_{int}$=0.065). 362 parameters. The structure was solved by direct methods and refined by full-matrix least squares on F. Final R1 [I>2σ (I)]=0.0892 and wR=0.1177 (all data); GOF=1.174.

Synthesis of Capsule-Type Compound ([$SO_4 \subset Ni_2$(m-bbitb)$_4$]$SO_4$)

A capsule-type compound ([$SO_4 \subset Ni_2$(m-bbitb)$_4$]$SO_4$) was synthesized using a nickel ion according to the following reaction scheme 2.

-Reaction Scheme 2-

A detailed description will now be made of the reaction scheme 2.

First, $NiSO_4 \cdot 6H_2O$ (39.4 mg, 0.15 mmol) was dissolved in water (30 mL) to obtain an aqueous solution of $NiSO_4 \cdot 6H_2O$.

Then, an m-bbitb solution in which m-bbitb (110 mg, 0.30 mmol) was dissolved in ethanol was prepared, the obtained m-bbitb solution was added to the aqueous solution of $NiSO_4 \cdot 6H_2O$, and the resultant was stirred at approximately 40° C. for several hours. A precipitate produced in the reaction solution was filtrated and removed, followed by gradually concentrating the filtrate under reduced pressure to obtain a green white solid. The obtained green white solid was collected by filtration and was dried under reduced pressure to obtain [$SO_4 \subset Ni_2$(m-bbitb)$_4$]$SO_4$ (yield of 80 mg, 0.044 mmol; (yield of 58%)).

The production of [$SO_4 \subset Ni_2$(m-bbitb)$_4$]$SO_4$ was confirmed by the following elemental analysis.

The elemental analysis was conducted using Euro EA3000 manufactured by Euro Vector.

—Elemental Analysis Results—

Calcd. for $C_{100}H_{96}Ni_{16}Ni_2O_8S_2$: C, 65.58; H, 5.28; N, 12.24.

Found: C, 65.65; H, 5.12; N, 12.36.

Production of [$SO_4 \subset Cu_2$(m-bbitb)$_4$]$SO_4$-Fixed Filter

[$SO_4 \subset Cu_2$(m-bbitb)$_4$]$SO_4$ (0.20 g, 0.10 mmol) was suspended in 40 mL of water. The suspension was passed through a syringe filter (manufactured by Lab Lab Company Co. Ltd., filter diameter of 40 mm, filter pore size of 0.2 mm) attached to a syringe, to fix [$SO_4 \subset Cu_2$(m-bbitb)$_4$]$SO_4$ on the syringe filter. Then, the syringe filter was dried at room temperature under reduced pressure for 24 hours to obtain the syringe filter on which [$SO_4 \subset Cu_2$(m-bbitb)$_4$]$SO_4$ was fixed (hereinafter also referred to as "[$SO_4 \subset Cu_2$(m-bbitb)$_4$]$SO_4$-fixed filter").

Example 2

Removal of Anion by Capsule-Type Compound ([$SO_4 \subset Cu_2$(m-bbitb)$_4$]$SO_4$)

Sodium perchlorate (61.2 mg, 0.5 mmol), sodium bromide (51.5 mg, 0.5 mmol), sodium nitrate (42.5 mg, 0.5 mmol), and sodium sulfate (71.0 mg, 0.5 mmol) were accurately measured respectively and were dissolved in ultrapure water (500 mL) at a water temperature of 30° C. to prepare an anion aqueous solution A in which the concentration of each anion ($ClO_4^-$, $Br^-$, $NO_3^-$, or $SO_4^{2-}$) was 1 mM.

Subsequently, $[SO_4 \subset Cu_2(m\text{-}bbitb)_4]SO_4$ (0.1967 g, 0.1 mmol) was accurately measured in a 100 mL conical beaker, 100 mL of the anion aqueous solution A prepared as described above was added thereto to make a water-based sample 1, and the water-based sample 1 was left while being kept at 30° C. by a thermostat.

Every 2 minutes in the period of 10 minutes or less after the addition of the above-described anion aqueous solution A, every 10 minutes in the period of more than 10 minutes and 30 minutes or less after the addition of the above-described anion aqueous solution, and every 30 minutes in the period of more than 30 minutes and 180 minutes or less after the addition of the above-described anion aqueous solution, 20 μL was measured from the water-based sample 1, the measured 20 μL of water-based sample 1 was diluted 25 times with 4800 μL of ultrapure water, and the concentration of each anion in the diluted water-based sample 1 was measured using ion chromatography. The ion chromatography was conducted using Metrohm Compact IC 861 ion chromatography manufactured by Metrohm. The progressions of the concentrations of the anions in the water-based sample 1 were determined from the measurement results.

Figure 2:
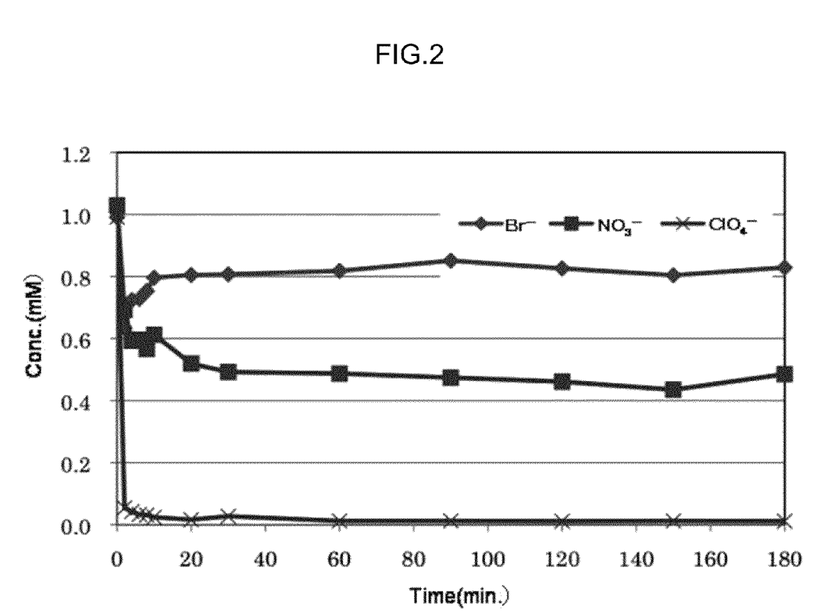
FIG. 2 is a graph that indicates the progression of anion concentration (for 180 minutes after addition of an anion aqueous solution A) in Example 2.

The progressions of the concentrations of the anions in the water-based sample 1 were indicated in Table 1 and FIG. 2.

TABLE 1

| Time (min) | $Br^-$ (mM) | $NO_3^-$ (mM) | $SO_4^{2-}$ (mM) | $ClO_4^-$ (mM) |
|---|---|---|---|---|
| 0 | 0.991 | 1.029 | 0.998 | 0.991 |
| 2 | 0.634 | 0.692 | 1.809 | 0.054 |
| 4 | 0.724 | 0.593 | 1.816 | 0.042 |
| 6 | 0.728 | 0.596 | 1.772 | 0.033 |
| 8 | 0.753 | 0.566 | 1.805 | 0.031 |
| 10 | 0.796 | 0.612 | 1.865 | 0.024 |
| 20 | 0.805 | 0.519 | 1.84 | 0.016 |
| 30 | 0.807 | 0.492 | 1.845 | 0.027 |
| 60 | 0.818 | 0.487 | 1.843 | 0.012 |
| 90 | 0.851 | 0.474 | 1.925 | 0.012 |
| 120 | 0.826 | 0.461 | 1.863 | 0.011 |
| 150 | 0.804 | 0.435 | 1.814 | 0.012 |
| 180 | 0.829 | 0.485 | 1.88 | 0.011 |

The "Time (min)" column in Table 1 and the horizontal axis in FIG. 2 represent lapse time (unit: min) from the addition of the above-described anion aqueous solution A. The "$Br^-$ (mM)" column, the "$NO_3^-$ (mM)" column, the "$SO_4^{2-}$ (mM)" column and the "$ClO_4^-$ (mM)" column in Table 1 as well as the vertical axis in FIG. 2 represent the concentration (unit: mM) of each anion in the water-based sample 1.

As indicated in Table 1 and FIG. 2, the concentrations of $Br^-$, $NO_3^-$, and $ClO_4^-$ were confirmed to be remarkably decreased after a lapse of 2 minutes from the addition of the anion aqueous solution A. Within 30 minutes after the addition of the anion aqueous solution A, the concentrations of $Br^-$, $NO_3^-$, and $ClO_4^-$ were decreased to around 0.8 mM, around 0.5 mM, and around 0.03 mM, respectively.

In Example 2, the concentration of $ClO_4^-$ was particularly remarkably decreased, and the $ClO_4^-$ concentration of 1 mM (about 100,000 ppb) was decreased to 0.02 mM or less (about 2,000 ppb or less) within a lapse time of 1 hour.

Further, since $SO_4^{2-}$ was increased with lapse time after the addition of the anion aqueous solution A, the counterion exchange of $SO_4^{2-}$ as a counter ion in $[SO_4 \subset Cu_2(m\text{-}bbitb)_4]SO_4$ with $Br^-$, $NO_3^-$, and $ClO_4^-$ was confirmed to occur.

Example 3

Removal of Anion by Capsule-Type Compound ($[SO_4 \subset Ni_2(m\text{-}bbitb)_4]SO_4$)

As a result of conducting an experiment on the removal of anions in the same manner as in Example 2 except that $[SO_4 \subset Cu_2(m\text{-}bbitb)_4]SO_4$ in Example 2 was changed to $[SO_4 \subset Ni_2(m\text{-}bbitb)_4]SO_4$, $[SO_4 \subset Ni_2(m\text{-}bbitb)_4]SO_4$ was confirmed to decrease the concentrations of the anions in the water-based sample as in the case of Example 2.

Example 4

Removal of Anion by $[SO_4 \subset Cu_2(m\text{-}bbitb)_4]SO_4$-Fixed Filter

Preparation of 6 mL of an aqueous sodium perchlorate solution (0.010 mM) containing 1000 ppb of perchlorate ion was carried out and the aqueous solution was passed through the $[SO_4 \subset Cu_2(m\text{-}bbitb)_4]SO_4$-fixed filter indicated as described above.

Using ion chromatography, the concentrations of perchlorate ions ($ClO_4^-$) contained in the aqueous sodium perchlorate solution were determined before and after passing through the $[SO_4 \subset Cu_2(m\text{-}bbitb)_4]SO_4$-fixed filter, respectively.

Figure 3:
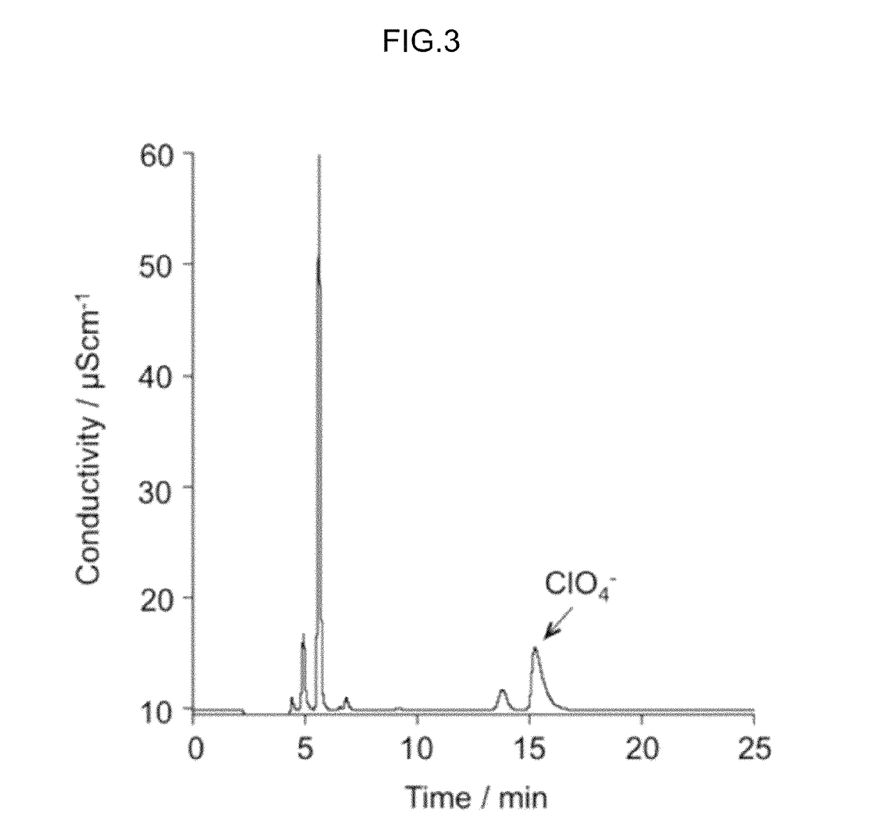
FIG. 3 is a chart of ion chromatography of an aqueous sodium perchlorate solution (before passing through [SO$_4 \subset$ Cu$_2$(m-bbitb)$_4$]SO$_4$-fixed filter) in Example 4.
Figure 4:
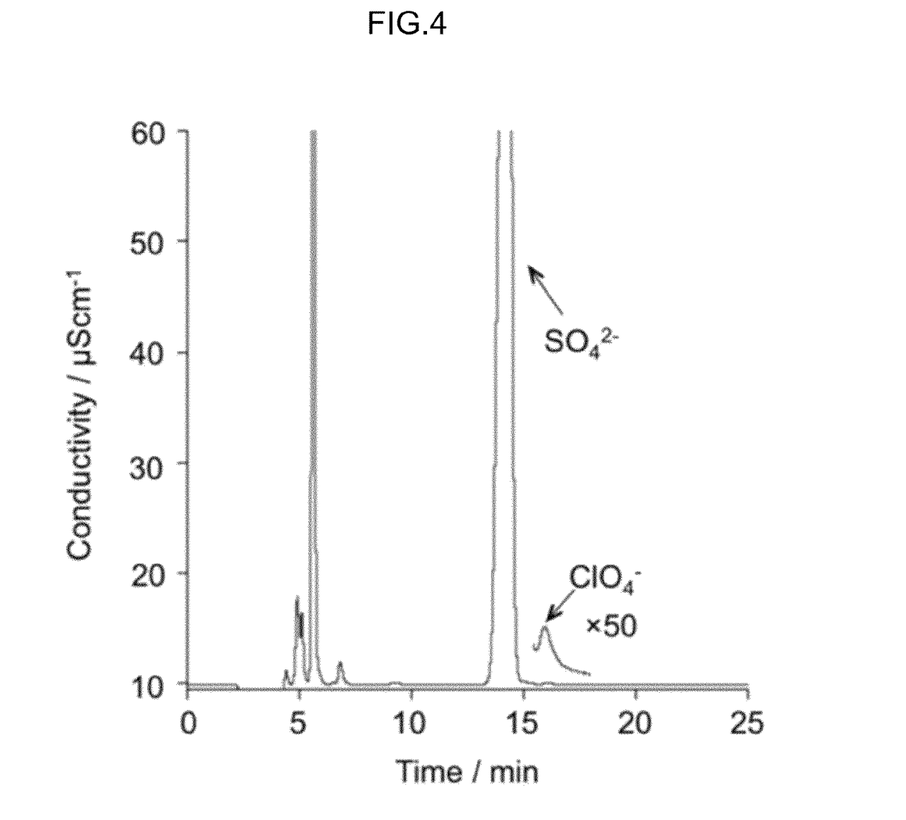
FIG. 4 is a chart of ion chromatography of an aqueous sodium perchlorate solution (after passing through [SO$_4 \subset$ Cu$_2$(m-bbitb)$_4$]SO$_4$-fixed filter) in Example 4.

FIG. 3 indicates a chart of the ion chromatography of the aqueous sodium perchlorate solution (before the passing through the $[SO_4 \subset Cu_2(m\text{-}bbitb)_4]SO_4$-fixed filter) while FIG. 4 indicates a chart of the ion chromatography of the aqueous sodium perchlorate solution (after the passing through the $[SO_4 \subset Cu_2(m\text{-}bbitb)_4]SO_4$-fixed filter).

The results of FIG. 3 and FIG. 4 revealed that the $ClO_4^-$ concentration of 1000 ppb before the passing through the $[SO_4 \subset Cu_2(m\text{-}bbitb)_4]SO_4$-fixed filter was changed to 12 ppb after the passing through the $[SO_4 \subset Cu_2(m\text{-}bbitb)_4]SO_4$-fixed filter.

Further, as indicated in FIG. 4, the intense peak of $SO_4^{2-}$ after the passing through the $[SO_4 \subset Cu_2(m\text{-}bbitb)_4]SO_4$-fixed filter was confirmed. It was confirmed from the result that the counterion exchange of $SO_4^{2-}$ as a counter ion in $[SO_4 \subset Cu_2(m\text{-}bbitb)_4]SO_4$ with $ClO_4^-$ was caused by the passing through the filter.

As described above, in Example 4, the concentration of $ClO_4^-$ was able to be decreased from 1000 ppb to 12 ppb only by the passing through the $[SO_4 \subset Cu_2(m\text{-}bbitb)_4]SO_4$-fixed filter. The targeted safety standard concentration value of perchlorate ion is currently set at 24.5 ppb or less in the United States Environmental Protection Agency (EPA), and the safety standard concentration was able to be achieved in a very short time in the Example 4.

Example 5

Removal of Iodide Ion by Capsule-Type Compound ($[SO_4 \subset Cu_2(m\text{-}bbitb)_4]SO_4$)

Sodium iodide (150 mg, 1 mmol) was accurately measured and was dissolved in ultrapure water (1000 mL) at a water temperature of 30° C. to prepare an iodide ion aqueous solution B at a concentration of 1 mM.

Subsequently, $[SO_4 \subset Cu_2(m\text{-}bbitb)_4]SO_4$ (0.1967 g, 0.1 mmol) was accurately measured in a 100 mL conical beaker, 100 mL of the iodide ion aqueous solution B prepared as described above was added thereto to make a water-based sample 2, and the water-based sample 2 was left while being kept at 30° C. by a thermostat.

Every 10 minutes in the period of 30 minutes or less after the addition of the above-described iodide ion aqueous solution B and every 30 minutes in the period of more than 30 minutes and 180 minutes or less after the addition of the above-described iodide ion aqueous solution B, 20 μL was measured from the water-based sample 2, the measured 20 μL of the water-based sample 2 was diluted 25 times with 4800 μL of ultrapure water, and the concentration of the iodide ion in the diluted water-based sample 2 was measured using ion chromatography. The progression of the concentration of the iodide ion in the water-based sample 2 was determined from the measurement results.

Figure 5:
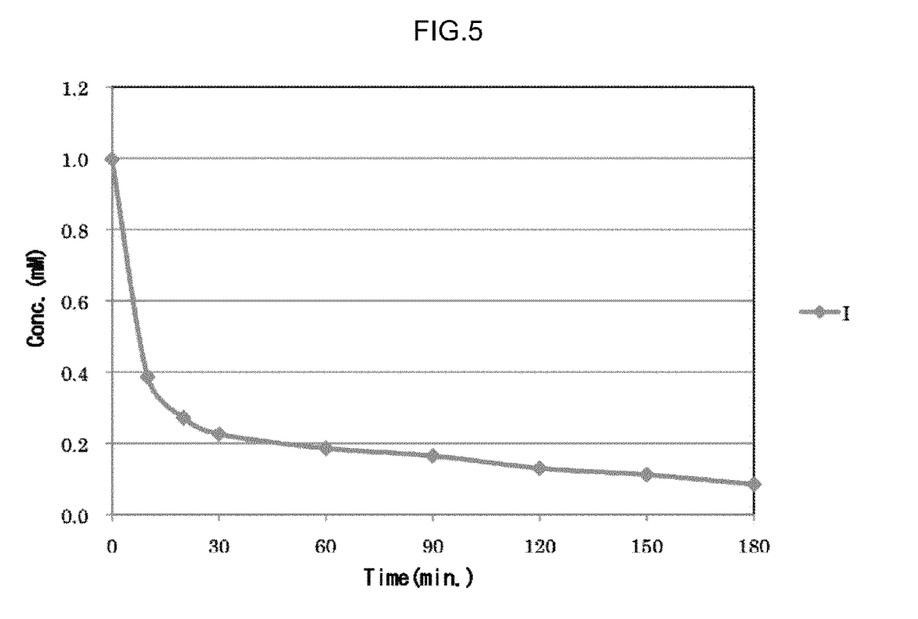
FIG. 5 is a graph that indicates the progression of iodide ion concentration (for 180 minutes after addition of an iodide ion aqueous solution B) in Example 5.

The progression of the concentration of the iodide ion in the water-based sample 2 was indicated in FIG. 5.

As indicated in FIG. 5, the concentration of $I^-$ was decreased to around 0.2 mM within 30 minutes after the addition of the iodide ion aqueous solution B and was decreased to 0.08 mM 180 minutes after the addition of the iodide ion aqueous solution B.

Comparative Example 1

Removal of Perchlorate Ion ($ClO_4^-$) by Ion Exchange Resin

A water-based sample 3 was prepared in the same manner as in Example 2 except that $[SO_4 \subset Cu_2(m\text{-bbitb})_4]SO_4$ (0.1967 g, 0.1 mmol) in Example 2 was changed to the same mass of an ion exchange resin (SR601188A530E (strongly basic anion exchange resin) manufactured by Purolite), and the progression of the concentration of each anion in the water-based sample 3 was measured in the same manner as in Example 2. Further consequently, the progression of the concentration of each anion in the water-based sample 3 was measured until 10000 minutes (about 1 week) after the addition of the anion aqueous solution A.

Figure 6:
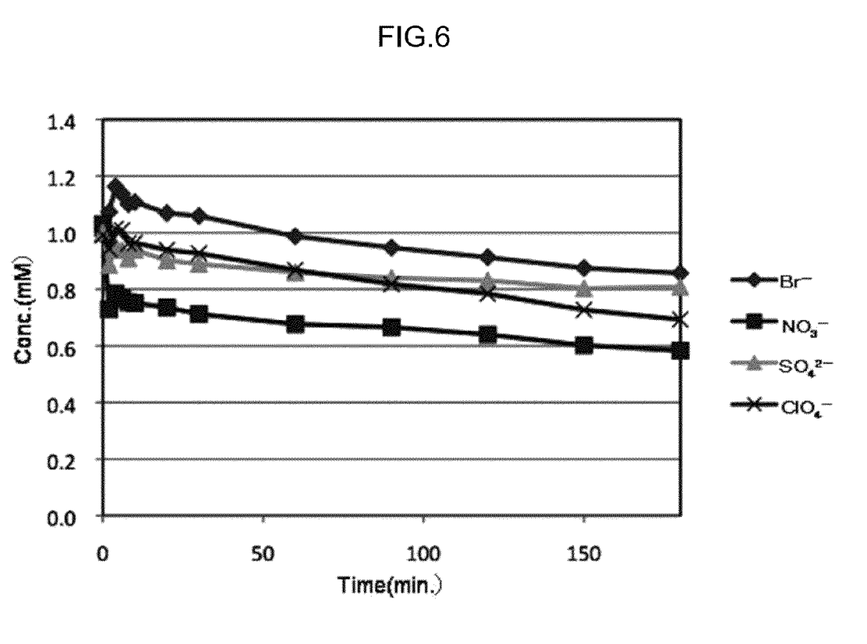
FIG. 6 is a graph that indicates the progression of anion concentration (for 180 minutes after addition of an anion aqueous solution A) in Comparative Example 1.
Figure 7:
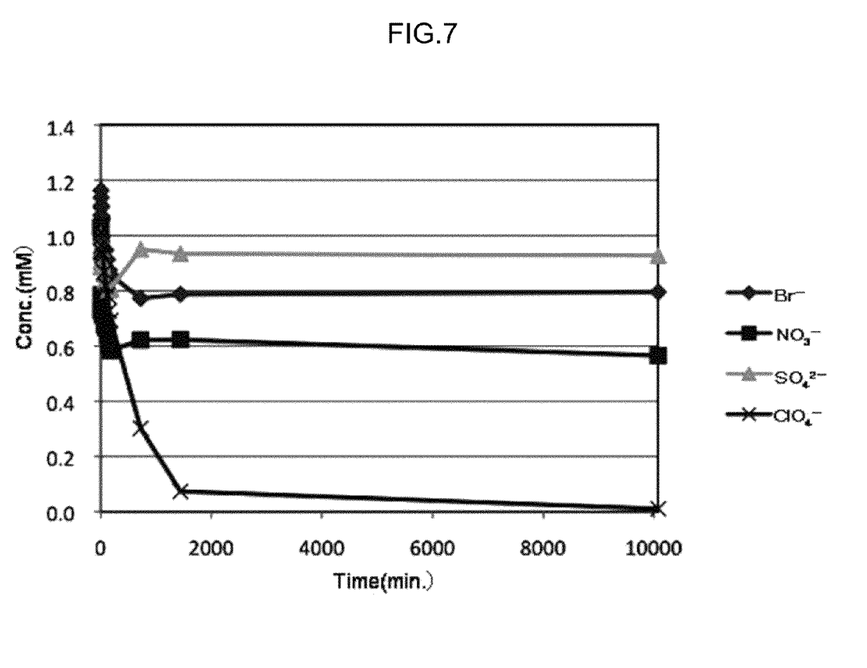
FIG. 7 is a graph that indicates the progression of anion concentration (for 10000 minutes after addition of an anion aqueous solution A) in Comparative Example 1.

The progressions of the concentrations of the anions in the water-based sample 3 are indicated in FIG. 6 (until 180 minutes after the addition of the anion aqueous solution A) and FIG. 7 (until 10000 minutes after the addition of the anion aqueous solution A).

The horizontal axes in FIG. 6 and FIG. 7 represent lapse time (unit: min) from the addition of the above-described anion aqueous solution A. The vertical axes in FIG. 6 and FIG. 7 represent the concentration (unit: mM) of each anion in the water-based sample 3.

As indicated in FIG. 6 and FIG. 7, in Comparative Example 1, longer time was needed for decreasing the concentration of each anion compared to Example 2.

For example, 180 minutes or more were needed for decreasing the concentration of $Br^-$ to around 0.8 mM, 150 minutes or more were needed for decreasing the concentration of $NO_3$ to around 0.6 mM, and 1000 minutes or more were needed for decreasing the concentration of $ClO_4^-$ to around 0.1 mM.

The examples of removing an anion using the capsule-type compound in which $M^1$ and $M^2$ in the formula (1) were $Cu^{2+}$ ($[SO_4 \subset Cu_2(m\text{-bbitb})_4]SO_4$) were indicated in Examples 2, 4 and 5 as described above, while the example of removing an anion using the capsule-type compound in which $M^1$ and $M^2$ in the formula (1) were $Ni^{2+}$ ($[SO_4 \subset Ni_2(m\text{-bbitb})_4]SO_4$) was indicated in Examples 3 as described above.

However, the present invention is not limited to the examples, and, for example, a capsule-type compound in which $M^1$ and $M^2$ in the formula (1) are $Fe^{2+}$ $Co^{2+}$, or $Zn^{2+}$, which can have planar tetracoordination, tetragonal pyramidal coordination, and octahedral coordination as in the case of $Cu^{2+}$ or $Ni^{2+}$, can be synthesized in the same manner as in $[SO_4 \subset Cu_2(m\text{-bbitb})_4]SO_4$ or $[SO_4 \subset Ni_2(m\text{-bbitb})_4]SO_4$ and can provide the same effect as that in $[SO_4 \subset Cu_2(m\text{-bbitb})_4]SO_4$ or $[SO_4 \subset Ni_2(m\text{-bbitb})_4]SO_4$.

While the examples of using the capsule-type compound in which $R^1$ to $R^{13}$ in the formula (1) were hydrogen atoms ($[SO_4 \subset Cu_2(m\text{-bbitb})_4]SO_4$ or $[SO_4 \subset Ni_2(m\text{-bbitb})_4]SO_4$) were indicated in Examples 1 to 5 as described above, a capsule-type compound in which at least one of $R^1$ to $R^{13}$ in the formula (1) is a methyl group can also be synthesized in the same manner as in $[SO_4 \subset Cu_2(m\text{-bbitb})_4]SO_4$ or $[SO_4 \subset Ni_2(m\text{-bbitb})_4]SO_4$ by changing a starting material (ligand). The obtained capsule compound has the same basic framework of the ligand as the basic framework of the ligand (m-bbitb) in $[SO_4 \subset Cu_2(m\text{-bbitb})_4]SO_4$ or in $[SO_4 \subset Ni_2(m\text{-bbitb})_4]SO_4$ and can therefore provide the same effect as that in $[SO_4 \subset Cu_2(m\text{-bbitb})_4]SO_4$ or $[SO_4 \subset Ni_2(m\text{-bbitb})_4]SO_4$.

While $ClO_4^-$, $Br^-$, and $NO_3^-$ were removed in Examples 2 and 3 as described above, $ClO_4^-$ was removed in Examples 4 as described above, and $I^-$ was removed in Examples 5 as described above, $BF_4^-$ of which the structure and properties are similar to those of $ClO_4^-$ can also be removed in the same manner as in $ClO_4^-$ by using the capsule-type compound of the present invention.

The entire disclosure of Japanese Application No. 2011-016235 is incorporated herein by reference.

All publications, patent applications, and technical standards described in this specification are incorporated herein by reference to the same extent as if each individual publication, patent application, or technical standard was specifically and individually indicated to be incorporated by reference.

The invention claimed is:

1. A capsule-type compound consisting of: a capsule-type divalent cation consisting of a capsule framework represented by the following formula (1) and a sulfate ion ($SO_4^{2-}$) encapsulated in the capsule framework; and a sulfate ion ($SO_4^{2-}$) as a counter ion to the capsule-type divalent cation:

wherein, in the formula (1), $R^1$, $R^2$, $R^3$, $R^4$, $R^5$, $R^6$, $R^7$, $R^8$, $R^9$, $R^{10}$, $R^{11}$, $R^{12}$, and $R^{13}$ each independently represents a hydrogen atom or a methyl group; in the formula (1), $M^1$ and $M^2$ each independently represents $Cu^{2+}$, $Fe^{2+}$, Ni$^{2+}$, Co$^{2+}$, or Zn$^{2+}$; and in the formula (1), a broken line represents a coordinate bond.

2. The capsule-type compound according to claim 1, wherein M$^1$ and M$^2$ are the same.

3. The capsule-type compound according to claim 1, wherein M$^1$ and M$^2$ are Cu$^{2+}$.

4. The capsule-type compound according claim 1, wherein R$^1$, R$^2$, R$^3$, R$^4$, R$^5$, R$^6$, R$^7$, R$^8$, R$^9$, R$^{10}$, R$^{11}$, R$^{12}$, and R$^{13}$ are all hydrogen atoms.

5. An anion removing agent comprising, as an active component, the capsule-type compound according claim 1.

6. A method for removing an anion, comprising a step of bringing a water-based sample containing water and at least one anion selected from the group consisting of ClO$_4^-$, BF$_4^-$, NO$_3^-$, Br$^-$, and I$^-$, and the capsule-type compound according to claim 1 into contact with each other to remove the anion from the water-based sample.

7. The method for removing an anion according to claim 6, wherein the water-based sample contains at least ClO$_4^-$.

\* \* \* \* \*